United States Patent
Yang et al.

(10) Patent No.: US 9,061,092 B2
(45) Date of Patent: Jun. 23, 2015

(54) METHOD FOR FABRICATING MEDICAL DEVICES WITH POROUS POLYMERIC STRUCTURES

(71) Applicant: ABBOTT CARDIOVASCULAR SYSTEMS INC., Santa Clara, CA (US)

(72) Inventors: Kumin Yang, Winchester, CA (US); Neftali Fernandez, Moreno Valley, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 157 days.

(21) Appl. No.: 13/622,950

(22) Filed: Sep. 19, 2012

(65) Prior Publication Data

US 2013/0017313 A1 Jan. 17, 2013

Related U.S. Application Data

(62) Division of application No. 12/163,845, filed on Jun. 27, 2008, now Pat. No. 8,298,466.

(51) Int. Cl.

| | |
|---|---|
| *A61L 31/10* | (2006.01) |
| *A61L 31/14* | (2006.01) |
| *A61L 31/16* | (2006.01) |
| *B29C 47/00* | (2006.01) |
| *B29L 31/00* | (2006.01) |
| *B29K 105/04* | (2006.01) |
| *A61F 2/89* | (2013.01) |

(52) U.S. Cl.
CPC .......... *A61L 31/148* (2013.01); *B29C 47/0004* (2013.01); *B29C 47/0023* (2013.01); *B29L 2031/7542* (2013.01); *B29K 2105/04* (2013.01); *A61L 31/10* (2013.01); *A61L 31/146* (2013.01); *A61L 31/16* (2013.01); *A61L 2400/18* (2013.01); *A61L 2420/02* (2013.01); *A61F 2/89* (2013.01)

(58) Field of Classification Search
CPC .............. B29C 71/0009; B29C 45/174; B29C 45/1701; B29C 45/1703; B29C 37/0028; B29C 37/0025; B29C 47/00
USPC ........... 424/423; 264/211.19, 211.13, 211.16, 264/82, 46.1, 139, 162; 427/2.1, 2.15
See application file for complete search history.

(56) References Cited

U.S. PATENT DOCUMENTS

| | | |
|---|---|---|
| 5,059,211 A | 10/1991 | Stack et al. |
| 5,085,629 A | 2/1992 | Goldberg et al. |
| 5,306,286 A | 4/1994 | Stack et al. |
| 5,443,458 A | 8/1995 | Eury |
| 5,500,013 A | 3/1996 | Buscemi et al. |
| 5,551,954 A | 9/1996 | Buscemi et al. |
| 5,618,298 A | 4/1997 | Simon |
| 5,629,077 A | 5/1997 | Turnlund et al. |
| 5,670,161 A | 9/1997 | Healy et al. |

(Continued)

*Primary Examiner* — Jacob Thomas Minskey
(74) *Attorney, Agent, or Firm* — Squire Patton Boggs (US) LLP (57) ABSTRACT

Medical articles with porous polymeric structures and methods of forming thereof are disclosed. The porous structure can have pores sizes that are nanoporous or greater than nanoporous. The porous structure can be a coating or layer of a medical device such as a stent, stent graft, catheter, or lead for pacemakers or implantable cardioverter defibrillators. Additionally, the body of the medical device can be a porous polymeric structure. The porous structure can be made from bioabsorbable polymers. The porous structures can be formed by contacting a polymer with a supercritical fluid.

7 Claims, 8 Drawing Sheets

(56) References Cited

U.S. PATENT DOCUMENTS

| | | | |
|---|---|---|---|
| 5,674,286 A | 10/1997 | D'Alessio et al. | |
| 5,728,152 A | 3/1998 | Mirsch, II et al. | |
| 5,766,710 A | 6/1998 | Turnlund et al. | |
| 5,935,506 A | 8/1999 | Schmitz et al. | |
| 6,423,092 B2 | 7/2002 | Datta et al. | |
| 6,503,427 B1 | 1/2003 | Yamamoto et al. | |
| 6,593,384 B2 | 7/2003 | Anderson et al. | |
| 6,626,939 B1 | 9/2003 | Burnside et al. | |
| 6,652,582 B1 | 11/2003 | Stinson | |
| 6,709,452 B1 | 3/2004 | Valimaa et al. | |
| 6,747,121 B2 | 6/2004 | Gogolewski | |
| 6,884,251 B2 | 4/2005 | Spence et al. | |
| 6,972,025 B2 | 12/2005 | WasDyke | |
| 6,997,948 B2 | 2/2006 | Stinson | |
| 7,011,678 B2 | 3/2006 | Tenerz et al. | |
| 7,022,334 B1 | 4/2006 | Ding | |
| 7,044,965 B1 | 5/2006 | Spielberg | |
| 7,081,133 B2 | 7/2006 | Chinn et al. | |
| 7,094,260 B2 | 8/2006 | Jing et al. | |
| 7,108,716 B2 | 9/2006 | Burnside et al. | |
| 7,128,755 B2 | 10/2006 | Su et al. | |
| 7,147,659 B2 | 12/2006 | Jones | |
| 7,163,562 B2 | 1/2007 | Datta et al. | |
| 7,166,134 B2 | 1/2007 | Datta et al. | |
| 7,169,187 B2 | 1/2007 | Datta et al. | |
| 7,285,287 B2 | 10/2007 | Williams et al. | |
| 7,649,027 B2 | 1/2010 | Imai | |
| 8,298,466 B1 * | 10/2012 | Yang et al. | 264/211.19 |
| 2001/0037860 A1 | 11/2001 | Morita | |
| 2002/0004060 A1 | 1/2002 | Heublein et al. | |
| 2003/0104030 A1 * | 6/2003 | Igaki et al. | 424/426 |
| 2003/0153971 A1 | 8/2003 | Chandrasekaran | |
| 2003/0153972 A1 | 8/2003 | Helmus | |
| 2004/0071861 A1 | 4/2004 | Mandrusov et al. | |
| 2004/0088041 A1 | 5/2004 | Stanford | |
| 2004/0093066 A1 | 5/2004 | Durcan | |
| 2004/0220660 A1 | 11/2004 | Shanley et al. | |
| 2004/0249443 A1 | 12/2004 | Shanley et al. | |
| 2004/0260386 A1 | 12/2004 | Shalaby | |
| 2005/0019404 A1 | 1/2005 | Sung et al. | |
| 2005/0043783 A1 | 2/2005 | Amis et al. | |
| 2005/0060020 A1 | 3/2005 | Jenson | |
| 2005/0131126 A1 | 6/2005 | Yang et al. | |
| 2005/0137678 A1 | 6/2005 | Varma | |
| 2005/0222671 A1 | 10/2005 | Schaeffer et al. | |
| 2005/0228477 A1 | 10/2005 | Grainger et al. | |
| 2005/0234538 A1 | 10/2005 | Litvack et al. | |
| 2005/0267565 A1 | 12/2005 | Dave et al. | |
| 2005/0283224 A1 | 12/2005 | King | |
| 2006/0052859 A1 | 3/2006 | Igaki | |
| 2006/0058835 A1 | 3/2006 | Murayama et al. | |
| 2006/0066012 A1 | 3/2006 | Yang et al. | |
| 2006/0127442 A1 * | 6/2006 | Helmus | 424/423 |
| 2006/0142541 A1 | 6/2006 | Hossainy | |
| 2006/0177480 A1 | 8/2006 | Sung et al. | |
| 2006/0190076 A1 | 8/2006 | Taheri | |
| 2006/0198869 A1 | 9/2006 | Furst et al. | |
| 2006/0271168 A1 | 11/2006 | Kleine et al. | |
| 2006/0286138 A1 | 12/2006 | Malshe et al. | |
| 2006/0287710 A1 | 12/2006 | Lendlein et al. | |
| 2007/0009564 A1 * | 1/2007 | McClain et al. | 424/423 |
| 2007/0014831 A1 | 1/2007 | Sung et al. | |
| 2007/0038292 A1 | 2/2007 | Danielpour | |
| 2007/0043434 A1 | 2/2007 | Meerkin et al. | |
| 2007/0050009 A1 | 3/2007 | Flanagan | |
| 2007/0050018 A1 | 3/2007 | Wainwright | |
| 2007/0055364 A1 | 3/2007 | Hossainy et al. | |
| 2007/0197744 A1 | 8/2007 | Schadler et al. | |
| 2007/0213838 A1 * | 9/2007 | Hengelmolen | 623/23.71 |
| 2009/0023830 A1 | 1/2009 | Imai | |
| 2009/0048659 A1 | 2/2009 | Weber et al. | |
| 2009/0181295 A1 | 7/2009 | Usami et al. | |
| 2009/0287295 A1 | 11/2009 | Contiliano et al. | |
| 2009/0287300 A1 | 11/2009 | Dave et al. | |

\* cited by examiner

METHOD FOR FABRICATING MEDICAL DEVICES WITH POROUS POLYMERIC STRUCTURES

This application is a divisional application of U.S. patent application Ser. No. 12/163,845 which was filed on Jun. 27, 2008, which is incorporated by reference herein.

BACKGROUND OF THE INVENTION

1. Field of the Invention

This invention relates to medical devices including porous polymeric structures.

2. Description of the State of the Art

This invention relates to various kinds of medical devices including structures made from polymers. Such medical devices include, but are not limited to, radially expandable prostheses, such as stents and stent grafts, catheters, and leads for pacemakers and implantable cardioverter defibrillators (ICD).

Radially expandable endoprostheses are adapted to be implanted in a bodily lumen. An "endoprosthesis" refers to an artificial device that is placed inside the body. A "lumen" refers to a cavity of a tubular organ such as a blood vessel. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment.

"Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of requirements such as the radial strength necessary to withstand the structural loads, namely radial compressive forces, imposed on the stent as it supports the walls of a vessel. Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment).

Additionally, a medicated stent may be fabricated by coating the surface of either a metallic or polymeric scaffolding with a polymeric carrier that includes an active agent or drug. Polymeric scaffolding may also serve as a carrier of an active agent or drug.

Furthermore, it may be desirable for medical devices, such as stents, to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers can be configured to partially or completely erode away after the clinical need for them has ended.

SUMMARY OF THE INVENTION

Certain other embodiments of the present invention include a method of fabricating a stent, comprising: conveying a bioabsorbable polymer through an extruder; disposing a fluid into the extruder, wherein the fluid is supercritical in at least a portion of the extruder, the supercritical fluid being mixed or dispersed within the polymer; coextruding a tube comprising two layers, at least one layer being a porous layer formed from the polymer in the extruder, the porous structure of the layer being formed when the fluid becomes subcritical; and forming a stent pattern in the coextruded tube.

DETAILED DESCRIPTION OF THE INVENTION

Embodiments of the present invention relate to medical devices having porous bioabsorbable polymeric structures or portions. Such structures can also be referred to as polymeric foam structures. The embodiments of the methods of forming the porous foam structures include impregnating, mixing, or dispersing a supercritical fluid in a polymer. A thermodynamic instability is then induced in the fluid which results in the formation of cells or pores in the polymer.

The polymeric structures and methods of fabrication described herein are generally applicable to formation of porous polymeric structures for any medical device. In particular, the methods can be applied to tubular medical devices such as self-expandable stents, balloon-expandable stents, stent-grafts, catheters, and various kinds of electrodes or leads for electrical cardiac medical devices, such as pacemakers and implantable cardioverter defibrillators (ICD).

Figure 1:
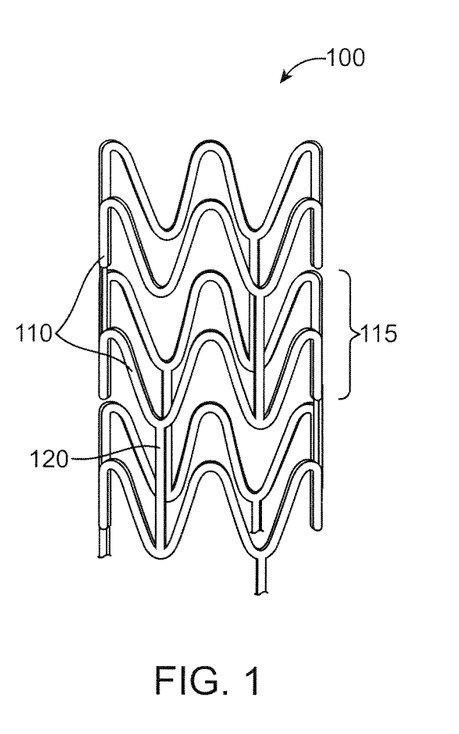
FIG. 1 depicts a stent.

An exemplary structure of a stent is shown in FIG. 1. FIG. 1 depicts a stent 100 which is made up of struts 110. Stent 100 has interconnected cylindrical rings 115 connected by linking struts or links 120. The embodiments disclosed herein are not limited to fabricating stents or to the stent pattern illustrated in FIG. 1. The embodiments are easily applicable to other stent patterns and other devices. The variations in the structure of patterns are virtually unlimited.

The embodiments are easily applicable to other patterns and other devices. The variations in the structure of patterns are virtually unlimited. A stent such as stent 100 may be fabricated from a tube by forming a pattern in the tube with a technique such as laser cutting or chemical etching.

Furthermore, stents and other medical devices have been designed for the localized delivery of a therapeutic agent. A medicated stent may be constructed by coating the device or substrate with a coating material containing a therapeutic agent. The substrate of the device may also contain a therapeutic agent. As described in more detail below, certain embodiments of the present invention include impregnating a therapeutic agent within the pores of the polymeric structure of a medical device.

In the various embodiments of the present invention, the porous polymeric structure of a medical device can be made partially or completely from a biodegradable or bioabsorbable. In other embodiments, the porous polymeric structures can also be made of biostable polymers. In general, a polymer for use in fabricating a medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes. In some treatment situations, a degradation time of less than 2 years may be desirable, for example, between 6 and 14 months, or more narrowly, between 8 and 12 months. Degradation time refers to the time for complete erosion of an absorbable structure from an implant site.

Many bioabsorbable polymers that are candidates for use in medical devices degrade through hydrolytic mechanisms. Common examples of such biodegradable polymers are poly (hydroxy acids) such as poly(L-lactide) (PLLA), poly(DL-lactic acid) (PDLA), polyglycolide, polycaprolactone, polyanhydrides, polyarylates, and copolymers thereof such as poly(glycolide-co-lactide) (PLGA).

Various embodiments of the present invention include medical devices having porous bioabsorbable polymeric structures. The porous structure formed can be characterized by several properties including, but not limited to, pore size, porosity, and open cell or closed cell structure. Open cells refer to pores that are connected to each other and form an interconnected network. Closed cells refer to cells that are not interconnected.

Porous bioabsorbable polymeric structures can be useful for controlling drug release and controlling degradation rate of a structure. With respect to drug release, drug release rate and content can be a function of the porosity. As porosity increases, the amount of drug that can be loaded into a structure increases. Additionally, the drug release rate can be influenced by porosity. Furthermore, degradation rate of a polymer structure can be controlled by porosity since degradation rate depends on moisture content or uptake of the structure. Thus, porosity of a porous structure can be modified to obtain selected drug release rate from, drug loading in, and degradation rate of a bioabsorbable polymeric structure.

The pore size can be controlled by adjusting or optimizing processing conditions during pore formation. In certain embodiments, the porous structures can be nanoporous. Nanoporous structures refer to pore sizes in the nanometer range, or less 1000 nm or 1 μm. In particular, nanoporous structures have pores with sizes of less than 2 nm ("microporous"), 2-50 nm ("mesoporous"), 50-1000 nm ("macroporous"). A majority, all, or substantially all of the pores can be in the nanoporous range. The definitions of microporous, mesoporous, and macroporous are set out by the International Union of Pure and Applied Chemistry (IUPAC). The porous structures can additionally have pores greater than 1 μm, in particular, 1-10 μm, 10-100 μm, or greater than 100 μm.

Certain embodiments can include stent with a stent body or scaffolding with a coating disposed above at least a portion of the stent body in which the coating is composed of a porous bioabsorbable polymer. In these embodiments, the stent body or scaffolding can be formed of a metal, a nonporous polymer, or both. A nonporous polymeric body or scaffolding can be formed of a bioabsorbable polymer, biostable polymer, or both. In exemplary embodiments, the stent body or scaffolding can be made from a semicrystalline bioabsorbable polymer with a Tg above human body temperature that remains relatively stiff at human body temperature. Exemplary polymers include PLLA, PLGA, and copolymers thereof.

The body or scaffolding of a stent is generally primarily responsible for providing mechanical support to walls of a bodily lumen once the stent is deployed within the bodily lumen. A stent body or scaffolding, for example, as pictured in FIG. 1, can refer to a stent structure with an outer surface to which no coating or layer of material different from that of which the structure is manufactured. If the body is manufactured by a coating process, the stent body can refer to a state prior to application of additional coating layers of different material. "Outer surface" means any surface however spatially oriented that is in contact with bodily tissue or fluids. A stent body, scaffolding, or substrate can refer to a stent structure formed by laser cutting a pattern into a tube or a sheet that has been rolled into a cylindrical shape.

As indicated above, the coating is disposed above at least a portion of the surface of the stent body or scaffolding. "Above" refers to over, but not necessarily in contact with. In some embodiments, the coating is disposed over an entire surface of the body or scaffolding, i.e., a luminal surface, abluminal surface, and sidewall surfaces of the structural elements of the stent.

Figure 2A:
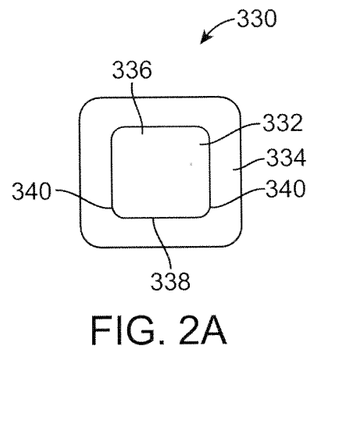
FIGS. 2A-B depict cross-sections of a stent strut with a coating.
Figure 2B:
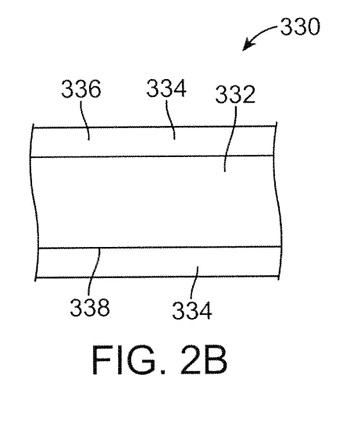

FIGS. 2A-B depict cross-sections of a stent strut 330 normal to and parallel to an axis of strut 330, respectively. A metal or polymeric body 332 has a porous polymer coating 334 over an abluminal surface 336, a luminal surface 338, and sidewall surfaces 340 of body 332.

In some embodiments, a therapeutic agent can be disposed or impregnated within the porous coating. Upon implantation of the stent, the agent can be released into a bodily lumen either through diffusion or degradation of the porous coating. Therapeutic agents can include, but are not limited to, anti-proliferative agents, anti-inflammatory agents, antibiotics, and antithrombotic agents. Anti-proliferative agents include, but are not limited to, Everolimus, Rapamycin, and/or derivatives thereof. Everolimus is available under the trade name Certican™, Novartis Pharma AG, Germany. An anti-inflammatory agent can include, without limitation, Clobetasol, which is available under the trade name Temovate™, Glaxosmithkline, UK. Antithrombotic agents include heparin.

In additional embodiments, the body or scaffolding can include coating layers in addition to the porous polymer layer. Such additional coating layers can be porous or nonporous. Additional coating layers may or may not include a therapeutic agent. In one embodiment, a nonporous polymer layer can be disposed above a porous medicated layer to control the diffusion of therapeutic agent from the medicated layer.

In further embodiments, a stent body or scaffolding can be composed of porous, bioabsorbable polymer. In such embodiments, the porous scaffolding can include a therapeutic agent disposed or impregnated within the porous stent body or scaffolding. The porous stent body or scaffolding can further include a nonporous, porous bioabsorbable polymer coating, or both.

In additional embodiments of the invention, a stent can have a structure including an abluminal layer, a luminal layer, and optionally an inner layer, with at least one of the layers being porous bioabsorbable polymer layer. Additionally, at least one of the layers can be metallic or a nonporous bioabsorbable polymer. The porous layer can optionally include a therapeutic agent.

An exemplary layered stent structure can include two layers with one layer being a porous medicated layer and a nonporous layer. In one embodiment, the nonporous layer can act as a body or scaffolding that is primarily responsible for maintaining vascular patency. For example, the nonporous layer can be 5-10, 10-50, 50-100, 100-1000 times, or more than 1000 times thicker than the abluminal and luminal layers. Alternatively, the nonporous layer can be 1-5 times that of the porous layer.

Figure 3A:
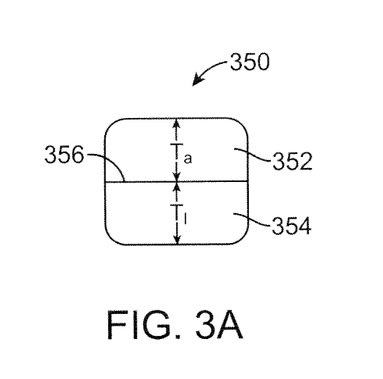
FIGS. 3A-B depict cross-sections of a stent strut composed of two layers.
Figure 3B:
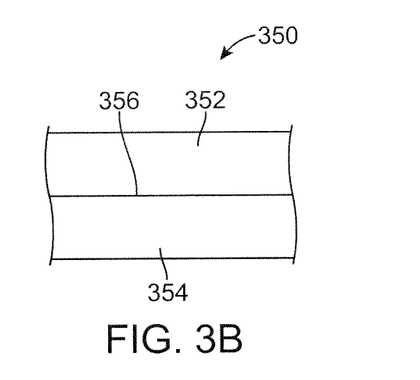

FIGS. 3A-B depict cross-sections of a stent strut 350 normal to and parallel to an axis of strut 350, respectively. Strut 350 has an abluminal layer 352 and a luminal layer 354 with line 356 depicting the boundary between the layers. Abluminal layer 352, luminal layer 354, or both can be porous bioabsorbable polymer. A thickness of the Ta of the abluminal layer and Tl of the luminal layer can be the same or different. As discussed above, in some embodiments, one of the layers can be thicker to serve the purpose of providing mechanical support to a lumen, while the other layer can include a therapeutic agent.

Another exemplary structure can include porous abluminal and luminal layers and a nonporous inner layer between the porous layers. In such a structure, the inner layer can act as a body or scaffolding that is primarily responsible for maintaining vascular patency. For example, the inner layer can be 5-10, 10-50, 50-100, 100-1000 times, or more than 1000 times thicker than the abluminal and luminal layers. The abluminal and luminal layer can further include a therapeutic agent.

In another exemplary structure, the inner layer can be porous and the abluminal and luminal layers can be nonporous. In such a structure the inner layer can be medicated and the abluminal and luminal layers can be primarily responsible for maintaining vascular patency.

Figure 4A:
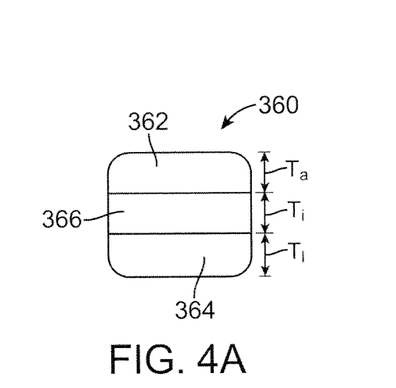
FIGS. 4A-B depict cross-sections of a stent strut composed of three layers.
Figure 4B:
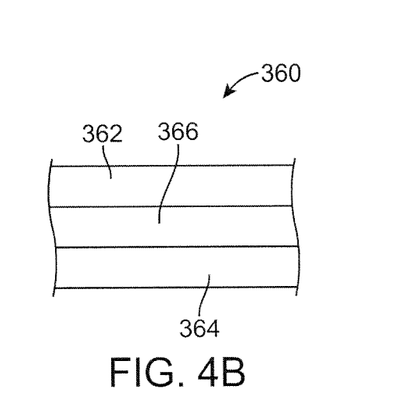

FIGS. 4A-B depicts cross-sections of a stent strut 360 normal to and parallel to an axis of strut 360, respectively. Strut 360 has an abluminal layer 362, a luminal layer 354, and an inner layer 366 with thicknesses, Ta, Tl, and Ti, respectively. At least one of the layers can be a nonporous bioabsorbable polymer layer, optionally including a therapeutic agent.

Further embodiments of the present invention include porous polymeric structures on electrical leads used with electrical cardiac devices. Cardiac rhythmic management devices such as pacemakers and ICD's monitor the heartbeat and provide electrical impulses or shocks to the heart through electrical leads/electrodes that are in direct contact with heart muscle. A pacemaker is a medical device which uses electrical impulses, delivered by such electrodes contacting the heart muscles, to regulate the beating of the heart. An ICD delivers an electrical shock through such leads to restore normal rhythm when life-threatening, irregular heartbeats are detected. In general, an ICD keeps the heart from beating too fast.

The leads or electrodes include one or more wires surrounded by an insulation, typically a flexible polymer. The presence of such leads in the body can lead to various complications or bodily disorders including endothelialization, infection, inflammation, and thrombosis (from intravenous leads). In certain embodiments, a cardiac device lead can include a porous polymeric layer including a therapeutic agent impregnated in the pores of the porous layer. The therapeutic agent(s) can be selected to treat one or more bodily disorders. The therapeutic agent can include, for example, an antiproliferative agent, an anti-inflammatory agent, antibiotics, or an anti-thrombotic agents.

The porous layer of the cardiac leads can be formed from a bioabsorbable or a biostable polymer. In particular, the porous layer can be formed from an elastomer conventionally used for cardiac leads, such as a silicone or polyurethane elastomer. Alternatively, the layer can be formed of a bioabsorbable polymer such as an elastomer. For example, bioabsorbable elastomeric polymers include polycaprolactone, polydioxanone, poly(hydroxy butyrate), and poly(trimethylene carbonate).

Figure 5A:
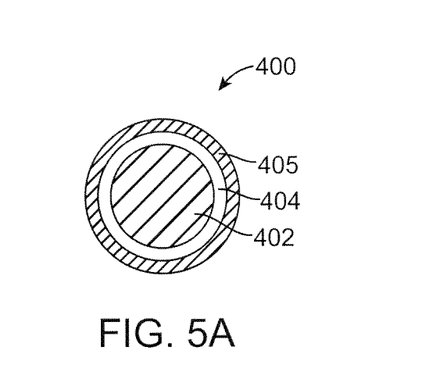
FIGS. 5A-B depicts cross-sections of a cardiac lead.
Figure 5B:
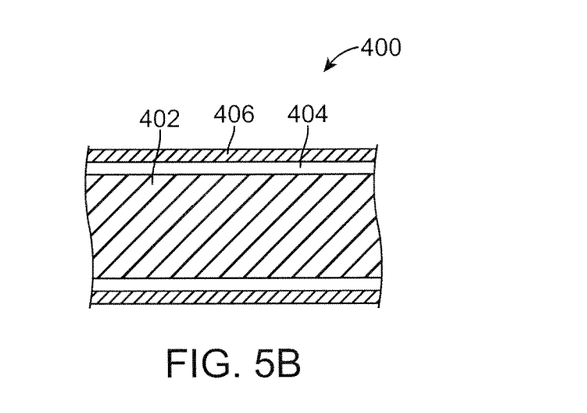

FIGS. 5A-B depict radial and axial cross-sections, respectively, of an exemplary cardiac lead 400. Cardiac lead 400 includes a tubular polymeric insulation sheath disposed over a wire 402. The sheath is composed of a nonporous inner polymeric layer 404 and a porous outer polymeric layer 405. The central lumen of the polymer sheath can be divided into two or more passageways or lumens to accommodate more than one wire.

Further embodiments of the present invention include a catheter having a porous polymer layer. In general, a catheter is a tube that can be inserted into a body cavity, duct, or vessel and is used in a number of medical applications. The presence of a catheter in the body can lead to various complications or disorders including endothelialization, infection, inflammation, and thrombosis. In certain embodiments, a catheter can include a porous polymer layer including a therapeutic agent impregnated in the pores of the porous layer. The porous layer can be formed of a bioabsorbable or biostable polymer.

In general, a porous polymeric structure or foam can be formed from a nonporous polymer composition using physical and/or chemical blowing agents. A particularly advantageous method of forming a porous polymeric structure includes the use of a supercritical fluid as a blowing agent. In such a technique, a polymeric foam structure is formed by impregnating a polymer with a supercritical fluid and inducing a thermodynamic instability through a temperature or pressure change to a subcritical state. The instability results in the formation of clusters or bubbles of higher density causing formation of pores in the polymer. Other methods known to those with skill the in art may also be used to form a porous polymer structure in the disclosed medical devices.

A "supercritical fluid" is any substance above its critical temperature, critical pressure, and critical density. Supercritical carbon dioxide may be used in the disclosed embodiments, although other supercritical fluids may be used. Carbon dioxide is non-toxic, non-flammable, chemically inert, completely recoverable, abundant and inexpensive. Carbon dioxide has properties that are between those of many liquids and gases. At room temperature and above its vapor pressure, carbon dioxide exists as a liquid with a density comparable to organic solvents but with excellent wetting properties and a very low viscosity. Above its critical temperature, pressure, and density (31° C., 73.8 bar, and 468 kg/m$^3$), carbon dioxide is in the supercritical state and has gas-like viscosities and liquid-like densities. Small changes in temperature or pressure cause dramatic changes in the density and viscosity.

In the present embodiments, the formation of porous polymeric structures in medical devices can be performed in batch or continuous modes of operation. A batch operation can include disposing a medical article having a polymeric portion in a chamber. For example, the chamber can be part of an autoclave that enables precise control of temperature and pressure within the chamber.

The medical article can include a medical device or parts thereof in various stages of manufacture. As discussed above, the medical article has a portion or structure that is composed of a polymer. The polymer structure can be nonporous or porous. In some embodiments, the medical article includes a porous polymer structure and a nonporous polymer structure.

In certain embodiments, the medical article can include a polymeric tube or a tube having a polymeric layer. Such a tube may be in a manufacturing stage prior to cutting a stent pattern. Additionally, a tube can be for use as a catheter or a sheath of a cardiac lead. Exemplary tubular medical articles include, but are not limited to:
- tube composed of a single homogeneous polymer layer,
- abluminal polymer layer and luminal polymer layer composed of the same or different polymers, and
- abluminal layer and luminal layer, one layer polymer and one layer metallic.

In addition, a medical article can include a stent having a polymeric portion. Exemplary stent structures include, but are not limited to:
- a stent body or scaffolding composed of a polymer,
- a stent body or scaffolding composed of a metal or polymer with a coating layer over abluminal, luminal, and sidewall surfaces,
- stent body or scaffolding with an abluminal layer and a luminal layer with at least one layer being composed of a polymer and another layer composed of the same or different polymer, and
- stent body or scaffolding with an abluminal layer and a luminal layer with one layer being a polymer layer and one layer being a metallic layer.

In the batch operation, embodiments of the method further include contacting the medical article in the chamber with a fluid at supercritical conditions. In particular, the supercritical fluid can be injected into the chamber. In such embodiments, prior to the contacting the medical article with the supercritical fluid, the temperature and pressure in the chamber may be adjusted to or above supercritical temperature (Tc) and pressure (Pc) of the fluid. The temperature of the chamber can be adjusted to a target temperature or temperature range above Tc that allows or facilitates impregnation of the supercritical fluid in the polymer of the medical article. The pressure can be adjusted to a target pressure or range up to a saturation pressure above Pc of the supercritical fluid in the polymer at the target temperature. The target pressure and temperature can be maintained for a selected time period which depends on the desired properties of the porous structure to be formed.

This temperature adjustment to the target temperature can be performed prior to injection of the supercritical fluid or alternatively, after injection of the supercritical fluid into the chamber. In exemplary embodiments, to facilitate impregnation of the supercritical fluid in the polymer, the target temperature can be above the glass transition temperature (Tg) or softening point (Ts) of the polymer. In exemplary embodiments, the target temperature can be up to 10° C. above, 10-50° C. above, 50-100° C. above, or more than 100° C. above the Tg or Ts of the polymer. In other embodiments, the target temperature can be up to 10° C. below, 10-30° C. below, 30-50° C. below, or more than 50° C. below the Tg or Ts of the polymer. In such embodiments, the supercritical fluid may be dissolved in the polymer so that the polymer and supercritical fluid are a single phase mixture. Tg's of some polymers that can be can be used are provided in Table 1.

TABLE 1

Melting points and glass transition temperatures of polymers.

| Polymer | Melting Point (° C.)[1] | Glass Transition Temp (° C.)[1] |
|---|---|---|
| PGA | 225-230[1] | 35-40 |
| PLLA | 173-178[1] | 60-65 |
| PDLA | Amorphous | 55-60 |
| PCL | 58-63[1] 60[2] | (−65)-(−60) |
| PDO | N/A | (−10)-0 |
| 85/15 PLGA | Amorphous | 50-55[1] |
| 75/25 PLGA | Amorphous | 50-55[1] |
| 65/35 PLGA | Amorphous | 45-50[1] |
| 50/50 PLGA | Amorphous | 45-50[1] |

[1]Medical Plastics and Biomaterials Magazine, March 1998.
[2]Science, Vol. 297 p. 803 (2002)

In the batch mode, the method further includes adjusting conditions in the chamber to subcritical conditions of the fluid to cause formation of pores in the polymer by the fluid. The conditions are adjusted in chamber to induce a thermodynamic instability in the fluid that result in the nucleation and growth of clusters of fluid in the polymer. The growth of the clusters induces the formation of cells or pores in the polymer, and thus a porous polymeric structure or polymeric foam. The thermodynamic instability can be induced through a decrease in pressure, temperature, or both to subcritical conditions in the chamber. For example, the chamber can be depressurized followed by cooling or the chamber can be cooled during the depressurizing.

"Nucleation" refers generally a process by which a homogeneous, single-phase solution of polymeric material, in which is dissolved molecules of a species that is a gas under ambient conditions, undergoes formations of clusters of molecules of the species that define "nucleation sites," from which cells will grow. That is, "nucleation" means a change from a homogeneous, single-phase solution to a mixture in which sites of aggregation of at least several molecules of fluid are formed. Nucleation defines that transitory state when gas, in solution in a polymer melt, comes out of solution to form a suspension of bubbles or clusters within the polymer.

Several process parameters can effect the properties of the porous polymer structure. These parameters include, but are not limited to, the target temperature and pressure during contacting the supercritical fluid, the contact time, the depressurization rate, and the cooling rate. It is expected that increasing the target pressure and contact time will increase the amount of supercritical fluid impregnated, thus resulting in smaller pores and higher cell density. Additionally, it is expected that a slower cooling rate will increase the degree of coalescence of clusters, thus resulting in larger pores. Increased coalescence may also result in a pore structure that are interconnected with an open cell structure.

In further embodiments, a drug can be impregnated within the pores of the porous polymer structure for delivery upon implantation of the polymer structure in a patient. In such embodiments, the drug can be impregnated with the supercritical fluid. The supercritical fluid for injection in the chamber can include a therapeutic agent dissolved or dispersed therein. In some embodiments, the therapeutic agent can be provided as a colloidal suspension in the supercritical fluid. The supercritical fluid with the dissolved or dispersed drug is injected into the chamber and both the supercritical fluid and therapeutic agent are impregnated within the polymer structure of the medical article. Upon adjustment to subcritical conditions in the chamber to form the pores, the therapeutic agent becomes impregnated in the pores that are formed.

Figure 6A:
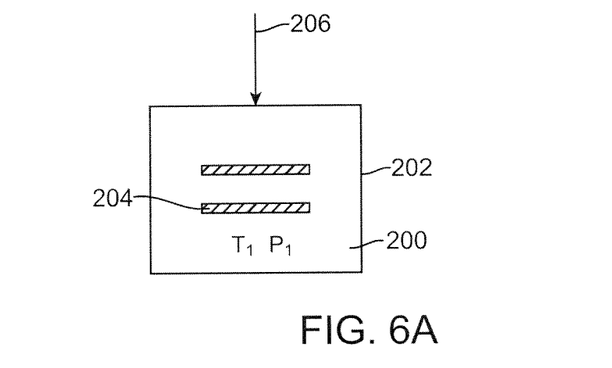
FIGS. 6A-B depict a chamber containing a polymeric medical article shown as a polymeric tube.
Figure 6B:
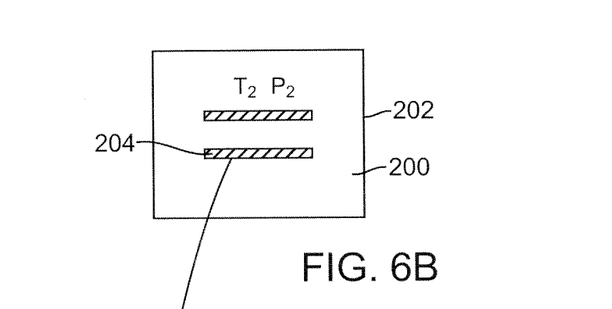
Figure 6C:
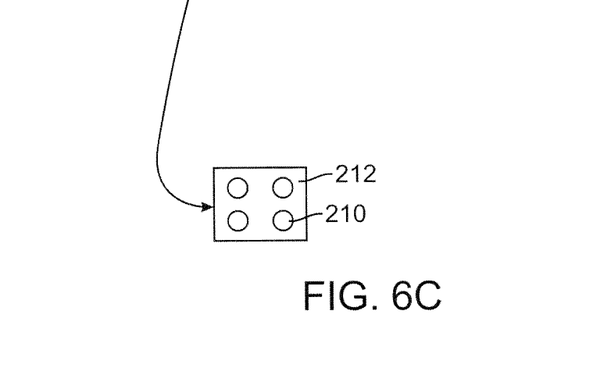
FIG. 6C depicts a blown up portion of the tube shown in FIGS. 6A-B.

FIGS. 6A-C depict a schematic illustration of a batch process for forming a porous polymeric structure of a medical article. FIG. 6A depicts a chamber 200 formed by walls 202 which contains a polymeric medical article shown as an axial cross-section of a polymeric tube 204. A supercritical fluid, optionally mixed with a therapeutic agent, is injected into chamber 200 as shown by an arrow 206. The temperature (T1) and pressure (P1) within chamber 200 are greater than Tc and Pc of the supercritical fluid. Chamber 200 is depressurized to a pressure P2 below Pc and cooled to a temperature T1 below Tc to induce pore formation. FIG. 6C shows a blown up portion of the tube 204 made up of a polymer matrix 212 with pores 210.

It is expected that formation of pores in a polymer structure of a medical article may cause the dimensions of the polymer structure to increase. In particular, a polymer tube or stent can radially expand during formation of pores resulting in an increase in an outer diameter of the stent. In certain embodiments, the increase in dimensions of the polymer structure can be prevented, reduced, or limited.

In such embodiments, a polymer tube in a chamber, as described above, can be disposed within a cylindrical mold to prevent, reduce, or limit radial expansion of the tube. The tube is positioned within the mold to limit or prevent radial expansion of the tube upon formation of the pores in the polymer tube. As the tube radially expands, an inner surface of the mold restrains or prevents radial expansion of the tube through contact with the outer surface of the tube.

In some embodiments, a tubular medical article, such as a polymer tube or stent, can be allowed to expand during pore formation without any restraint on the amount of expansion. In other embodiments, the medical article can be allowed to radially expand with the expansion limited to a target diameter by using a mold with an inner diameter that is equal to the target diameter. In additional embodiments, radial expansion of a tubular medical article can be prevented by disposing the tube in a mold having an inner diameter that is the same or approximately the same as the outer diameter of the tubular medical article so that there is a slip fit of the tubular medical article in the mold.

In general, deformation of a polymer can improve its mechanical properties, such as strength, along an axis of deformation. It has been observed that radial expansion of a tube can increase its radial strength. A stent formed from such a tube thus may have increased radial strength. The increase in radial strength is believed to be due at least in part to alignment of polymer chains along a circumference of the tube.

The degree of radial expansion, and thus induced radial orientation and strength, of a tube can be quantified by a radial expansion (RE) ratio:

RE ratio=Outside Diameter of Expanded Tube Original Inside Diameter of Tube

The degree of radial expansion can also be expressed as a percent expansion:

% Radial expansion=(RE ratio−1)×100%

In exemplary embodiments, the percent radial expansion can be 0-100%, 100-300%, 300-500%, or greater than 500%.

Figure 7A:
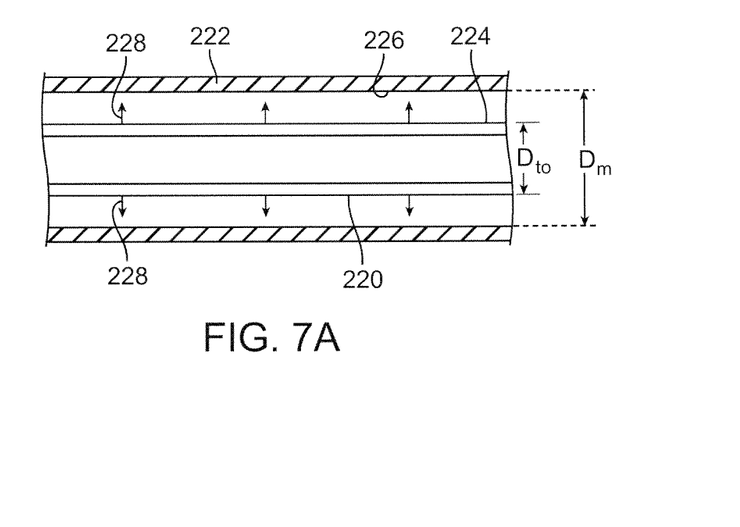
FIG. 7A depicts an axial cross-section of a tube disposed within a mold.
Figure 7B:
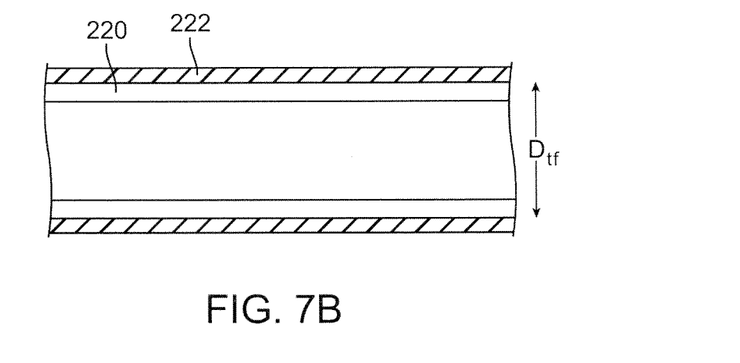
FIG. 7B depicts a radially expanded porous polymeric tube within a mold.

FIGS. 7A-B illustrate limiting radial expansion of a tube during pore formation. FIG. 7A depicts an axial cross-section of a tube 220 with an outer surface 224 disposed within a mold 222 with an inner surface 226. Tube 220 has an outer diameter D to prior to pore formation and mold 222 has an inner diameter Dm. During pore formation within a chamber (not shown), tube 220 has a tendency to radially expand as shown by arrows 228. FIG. 7B shows that inner surface 226 of mold 222 limits the radial deformation of tube 220 to Dtf (which is equal to Dm) through contact with outer surface 224 of tube 220.

In further embodiments, a porous polymer structure of a medical article can be formed through contact of a supercritical fluid with a polymer melt. Such embodiments include fabricating a medical article in a continuous operation using extrusion.

In general, extrusion refers to the process of conveying a polymer melt through an extruder and forcing the polymer melt through a die that imparts a selected shape to the polymer exiting the extruder. In the case of tubing extrusion, the polymer melt (extrudate) forced through the die forms a cylindrical film in the shape of a tube. The film is cooled and drawn axially to form the tubing.

An extruder generally includes a barrel through which a polymer melt is conveyed from an entrance to an exit port. The polymer is fed to an extruder barrel near its proximal end as a melt or in a solid form, for example, as a pellet from a hopper. The solid polymer is melted as it is conveyed through the barrel and mixed, for example, through interaction with rotating screws. The polymer in the extruder barrel is heated to temperatures above the melting temperature (Tm) of the polymer and exposed to pressures that are generally far above ambient. Since the viscosity decreases with temperature, the temperature is at a level that allows a desired flow rate of polymer through the extruder.

An extruder barrel also generally includes a breaker plate positioned at a distal end of the extruder barrel. A breaker plate is a thick metal disk with holes drilled through it. The breaker plate serves to create a back pressure in the barrel which facilitates uniform melting and mixing.

The polymer melt exits the distal end of the extruder barrel into a die. A die generally refers to a device having an orifice with a specific shape or design geometry that it imparts to a polymer melt pumped from an extruder. In the case of tubing extrusion, the die has a circular shaped orifice that imparts a cylindrical shape to the polymer melt exiting the die. The function of the die is to control the shape of the polymer melt by delivering polymer melt to the orifice. The polymer melt can be delivered at a selected temperature and pressure. The formed product exiting the die is cooled by passing it through a bath of fluid such as water. Representative examples of extruders for use with the present invention may include single screw extruders, intermeshing co-rotating and counter-rotating twin-screw extruders, and other multiple screw masticating extruders.

In embodiments of the present invention, a supercritical fluid is contacted with a polymer being conveyed through an extruder. In some embodiments, a supercritical fluid can be injected into the extruder and as the polymer is conveyed along the extruder barrel, the supercritical fluid is mixed or dispersed within the polymer. The supercritical fluid can be injected into the extruder an any point along the length of the extruder barrel that allows uniform or substantially uniform mixing of the fluid with the polymer. In general, a pressure and temperature gradient can exist in the extruder barrel between the proximal end and the distal end and through the extruder die. The mixture of the polymer and supercritical fluid can be a single or two phase composition.

In some embodiments, the pressure and temperature can be maintained above Tc and Pc along at least a portion of the extruder barrel and die to keep the fluid in a supercritical state. In other embodiments, a gas or liquid can be injected into the extruder barrel and conditions in the extruder barrel can transform the fluid to a supercritical state.

When a supercritical fluid is injected into the extruder, a pressure gradient is created within the extruder. In some embodiments, the proximal or upstream pressure can be 1,000-3,500 psi while the distal or downstream pressure can be 500-3,000 psi. The back plate or extruder die can control and maintain the pressure within the extruder from about 500-3,500 psi.

In some embodiments, a single-phase solution of supercritical fluid and polymer may be formed. The supercritical fluid tends to reduce the viscosity of the polymer. Thus, the polymer and supercritical fluid mixture can be processed at a lower temperature. The lower temperature processing is advantageous since molecular weight degradation of the polymer during processing is reduced. Exemplary processing temperatures in an extruder can be at or about Tm of the polymer, up to 10° C. above, 10-30° C. above, 30-50° C. above, or more than 50° C. above the Tm of the polymer. The Tm of some polymers that can be used are given in Table 1.

The method further includes inducing formation of pores in the polymer and fluid mixture. As above, a thermodynamic instability is created in the polymer and fluid mixture through a temperature, pressure, or both a temperature and pressure change in the polymer and fluid mixture to a subcritical state of the fluid. The instability results in the formation of clusters or bubbles of fluid within the polymer causing formation of pores in the polymer.

In some embodiments, the temperature and pressure of the polymer and fluid mixture can be maintained at supercritical conditions throughout the extruder barrel and die. In such embodiments, the polymer and fluid mixture is exposed to subcritical conditions as it exits the die, resulting in the formation of pores or cells in the polymer. In other embodiments, the polymer and fluid mixture in the extruder barrel is at supercritical conditions throughout and the polymer and fluid mixture is exposed to subcritical conditions in the extruder die. This results in the formation of pores in the polymer while the polymer is in the die. In additional embodiments, the polymer and fluid mixture can be exposed to supercritical conditions in the extruder barrel at a location along the axis of the barrel distal to the point of injection of the supercritical fluid. As a result, pores can form in the polymer while within the extruder barrel.

Figure 8:
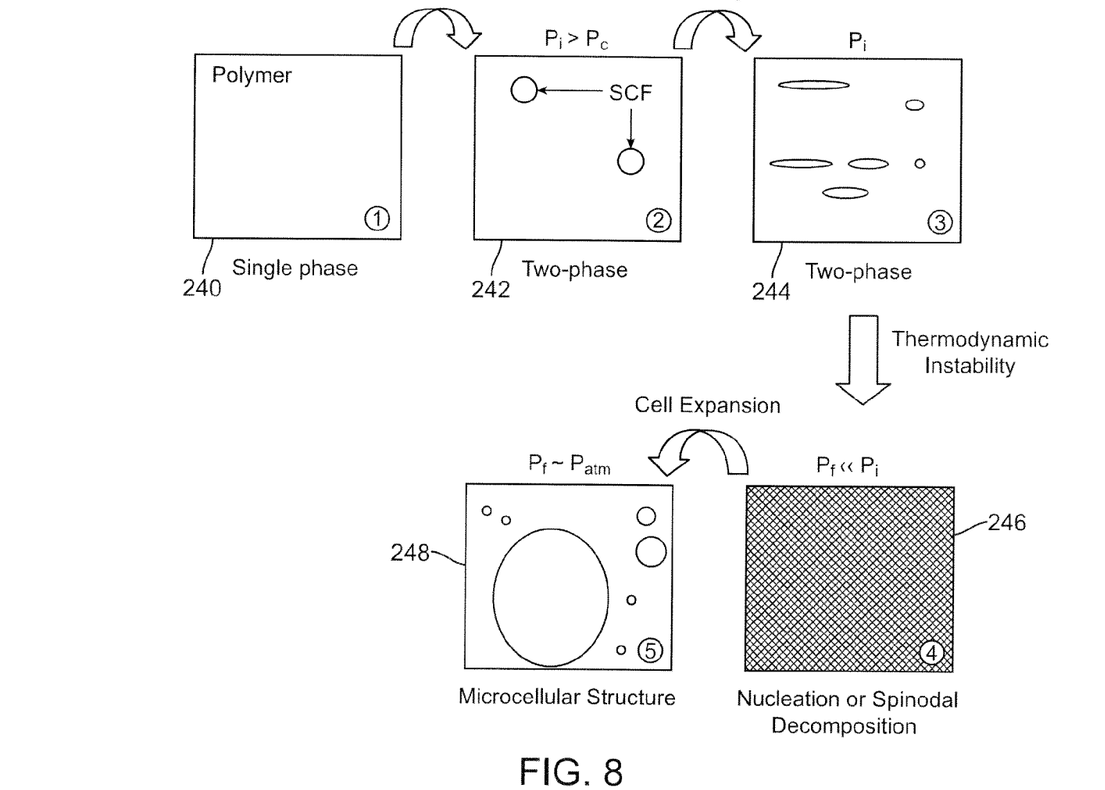
FIG. 8 depicts a schematic illustration of the formation of a porous polymer structure in a melt process.

FIG. 8 depicts a schematic illustration of the formation of a porous polymer structure in a melt process. A supercritical fluid is injected into a single phase polymer 240 to form a two phase system 242 of a polymer and supercritical fluid. The pressure (Pi) of two phase system 242 is greater than Pc. The two phase system 242 is mixed to form a dispersed system 244 with supercritical fluid dispersed within the polymer. A thermodynamic instability is induced by reducing the pressure to a pressure Pf below Pc to form a system 246 in which nucleation of clusters of subcritical fluid takes place within the polymer. A porous structure 248 forms due to expansion of the fluid with a Pf of the structure approximately Patm.

Figure 9:
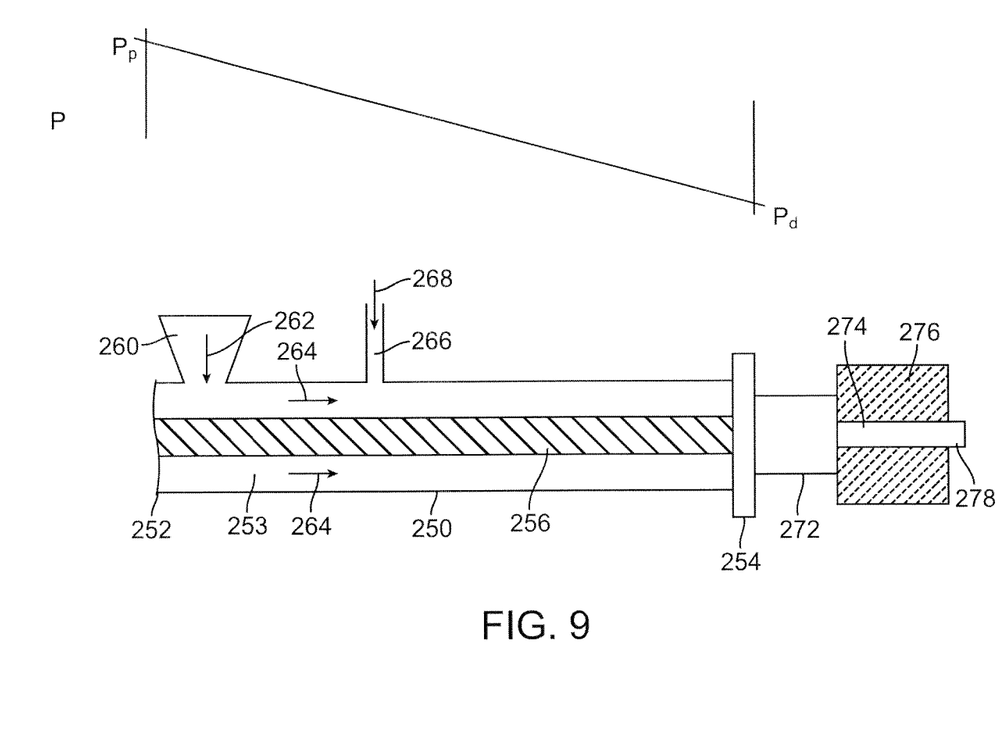
FIG. 9 depicts an extruder.

FIG. 9 depicts a schematic illustration of a continuous process for fabricating a medical article with a porous polymeric structure. FIG. 9 depicts an extruder 250 having an extruder barrel 253 with a proximal end 252 and a distal end 254 and a single rotating screw 256. A solid polymer is fed into extruder barrel 253 near proximal end 252 of extruder barrel 253 through a hopper 260 as shown by an arrow 262. Alternatively, a polymer melt rather than a solid polymer can be feed into extruder 250. The polymer is melted as it is conveyed, as shown by arrows 264, through barrel 253. A supercritical fluid is injected into barrel 253 through port 266 as shown by an arrow 268. Alternatively, the supercritical fluid can be injected with a polymer melt. A gas or liquid can also be injected at subcritical conditions and then transformed into a supercritical fluid at supercritical conditions after entering the extruder.

The polymer and fluid mixture exits barrel 253 through breaker plate 254 into extruder die 272. Polymer 274 exits extruder die 272 in the shape of a tube, for example, and is passed through a quench bath 276. Medical article 278 then passes out of quench bath 276.

FIG. 9 shows an exemplary pressure profile along the axis of the extruder with Pp and Pd being the pressure at the proximal and distal ends. As indicated above, the polymer and fluid mixture can be at supercritical conditions of the fluid in extruder barrel 253 and extruder die 272. In the case illustrated both Pp and Pd are above Pc. Pores are then formed in the polymer upon exiting extruder die 272 and passing into quench batch 274, which is at subcritical conditions. Alternatively, the polymer and fluid mixture can be exposed to subcritical conditions in extruder die 272 to form pores in the polymer. Another option is to expose the polymer and fluid mixture to subcritical conditions in extruder barrel 253 at a point distal to the point of injection of the supercritical fluid. In this case, Pc can be between Pp and Pd.

In further embodiments, a therapeutic agent can be impregnated within the pores of the porous polymer structure formed in the continuous extrusion process described above. In some embodiments, the drug can be dissolved or dispersed in the supercritical fluid. The supercritical fluid and therapeutic agent mixture can be injected through port 266 of extruder barrel 253, as described above. The therapeutic agent is then impregnated in the pores of the polymer when formed. The therapeutic agent can also be injected into extruder barrel 253 separately from the supercritical fluid.

Many therapeutic agents are subject to chemical degradation at high temperatures, for example, above 80-100° C. Therefore, such therapeutic agents may be chemically degraded upon injection into an extruder, as described above. To reduce or prevent such chemical degradation, some embodiments include impregnating the therapeutic agent into the polymer in the quench bath upon exiting the extruder. For example, the therapeutic agent can be dispersed or dissolved in the quench bath.

In other embodiments, a therapeutic agent can be impregnated into the pores of a porous polymer structure of a medical article after forming the porous polymer structure of the medical article, either through a continuous process or a batch process. One embodiment can include contacting a porous polymer structure of a medical article with a supercritical fluid mixed or dispersed with a therapeutic agent. A supercritical fluid and therapeutic agent mixture can be injected into a chamber including the medical article with a porous polymeric structure. The supercritical fluid and therapeutic agent mixture impregnates the pores of the porous polymeric structure. The supercritical fluid can then be removed from the chamber, leaving therapeutic agent impregnated in the pores of the polymeric structure.

Some embodiments can include reducing the extrusion temperature below a degradation temperature of the therapeutic agent. This can be performed through the use of gel or solvent extrusion. In gel or solvent extrusion, a polymer fluid including a polymer dissolved in a solvent is extruded at temperatures below the melting point of the polymer. Upon exiting the die, the polymer fluid is passed through a quench bath below ambient or room temperature to remove the solvent from the polymer to result in formation of a formed medical article.

In additional embodiments of the present invention, a tubular medical article can be formed having an abluminal layer and an luminal layer with at least one layer being composed of a porous polymer. In some embodiments, both of the layers can be porous polymers with the same or different pore structure properties, such as average pore size and porosity. One or both of the porous layers can include an impregnated therapeutic agent. In other embodiments, one of the layers is porous and the other is nonporous. In addition, the tubular medical article can also include one or more additional layers between the abluminal and luminal layers that are porous or nonporous.

A tubular medical article with abluminal and luminal layers as described above can be fabricated by a coating process. In one embodiment, a coating layer can be formed above an outer surface, an inner surface, or both of a porous polymeric tube made from the batch or continuous process described above. The coating layer can be formed by coating methods that involve application of a coating composition including a polymer dissolved in a solvent to a porous surface of the tube. The solvent is then removed through evaporation, leaving a nonporous polymer layer on the porous surface. The coating composition can be applied using various methods including spraying, dipping, or applying with an applicator such as a brush or sponge. The coating composition can also include a therapeutic agent to form a medicated nonporous layer.

In additional embodiments, a tubular medical article with abluminal and luminal layers, as described above, can be fabricated by coextrusion. Coextrusion refers to the process of extruding two or more materials through a single die with two or more orifices arranged so that the extrudates from the separate orifices merge and adheretogether into a laminar structure before cooling or chilling. Each material can be fed to the die from a separate extruder into separate orifices. In the case of tubing coextrusion, the die can include concentric circular slits through which the different materials exit to form a tube with two or more layers.

In embodiments of the present invention, an extruder conveys a polymer mixed with supercritical fluid, as described above, and supplies the mixture to a coextrusion die. One or more porous polymeric layers of a layered tube is formed from the extrudate. Pores can be formed in the polymer in the extruder, die, or upon exiting the die with the two or more orifices.

Figure 10A:
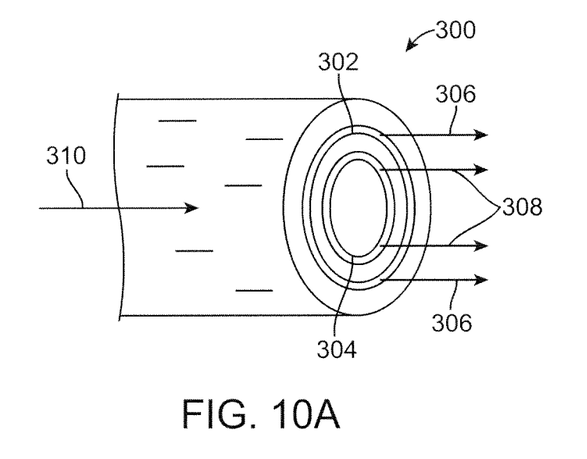
FIG. 10A depicts a die having two circular orifices.
Figure 10B:
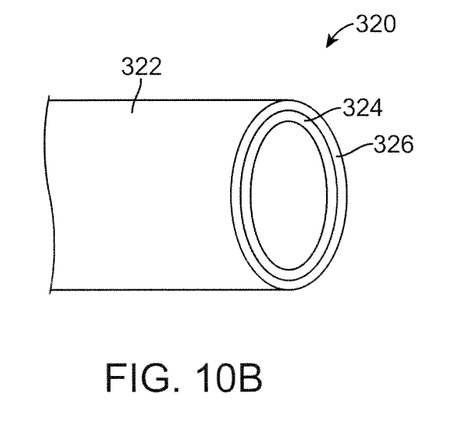
FIG. 10B depicts a coextruded tube.

In an exemplary embodiment, FIG. 10A depicts a die 300 having two circular orifices, an outer orifice 302 and an inner orifice 304. An extrudate including a polymer material of an outer layer can exit through outer orifice 302, as shown by arrows 306, while an extrudate corresponding to an inner layer can exit through inner orifice 304, as shown by arrows 308. One or both of the extrudates can include a polymer mixed with a supercritical fluid that allows formation of pores in the polymer. The extrudates are conveyed through die 300, in the direction of an arrow 310. The exiting extrudates merge and are welded together to form a cylindrical layered film which is cooled to form a tube. One or both of the layers can be a porous layer. FIG. 10B depicts a coextruded tube 320 with an outer surface 322, an inner layer 324, and an outer layer 326.

As indicated above, the batch and continuous processes can be used to fabricate various medical devices having a variety of structures. In particular, a batch or continuous process can be used to fabricate a tube with a polymeric foam structure. Further processing may be required to complete fabrication of the device.

A stent or stent graft with a porous polymeric body or scaffolding can be fabricated by making a porous polymeric tube with either a batch or a continuous process. A stent pattern is then cut into the porous body to form a stent body or scaffolding. FIG. 1 depicts an exemplary stent scaffolding structure. An exemplary porous polymeric stent body can be composed of all of substantially all PLLA or PLGA. Such a stent can further include a nonporous PDLA coating and optionally a therapeutic agent in the coating.

A stent or stent graft with a porous polymeric coating over a metal body or scaffolding is fabricated by applying the batch process to a metallic stent body or scaffolding having a coating layer over its abluminal, luminal, and sidewall surfaces.

Additionally, a stent or stent graft with a porous polymer coating, as show in FIGS. 2A-B, over a porous polymer body or scaffolding is fabricated by applying the batch process to a stent having a polymer body or scaffolding and a coating layer over its abluminal, luminal, and sidewall surfaces. In this case, body 332 in FIGS. 2A-B is a porous polymer body. An exemplary porous polymeric stent body can be composed of all of substantially all PLLA or PLGA. The porous coating can be composed of PDLA and optionally a therapeutic agent in the pores.

A stent structure including abluminal, luminal, and optionally one or more inner layers with at least one layer being a porous bioabsorbable polymeric layer can be fabricated by coextruding a tube having such a layered structure. A stent pattern is then cut into the tube to form a stent with the desired structure.

A stent body with porous abluminal and luminal layers can also be fabricated by forming a tube with nonporous inner and outer layers using coextrusion. The tube can then be subjected to the batch process above to form the porous layers. A stent can then be cut from the porous tube.

A stent with an abluminal and luminal layers with one layer being a porous polymeric layer and the other being a metallic layer can be fabricated by forming a porous polymeric tube by the continuous process and bonding the inner or outer surface of the polymeric tube to an outer or inner surface of a metallic tube. A stent pattern can then be cut in tube with metal and porous polymeric layers. Alternatively, a nonporous polymeric tube can be bonded to the metal tube. The tube or a stent cut from the tube can then be subjected to the batch process to form a porous polymeric layer.

Representative examples of polymers that may be used to fabricate a medical device according the embodiments described herein include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyether block amides, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as nylon 6,6 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in fabricating a medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

Representative examples of polymers that may be used to fabricate catheters include, but are not limited to, polyether block amides, polyamides, polyolefins, polyvinyl chloride, polyurethane, and polycarbonate.

Representative examples of metallic material or an alloy that may be used for fabricating medical devices include, but are not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum.

For example, a stainless steel tube or sheet may be Alloy type: 316L SS, Special Chemistry per ASTM F138-92 or ASTM F139-92 grade 2. Special Chemistry of type 316L per ASTM F138-92 or ASTM F139-92 Stainless Steel for Surgical Implants in weight percent. An exemplary weight percent may be as follows: Carbon (C): 0.03% max; Manganese (Mn): 2.00% max; Phosphorous (P): 0.025% max.; Sulphur (S): 0.010% max.; Silicon (Si): 0.75% max.; Chromium (Cr): 17.00-19.00%; Nickel (Ni): 13.00-15.50%; Molybdenum (Mo): 2.00-3.00%; Nitrogen (N): 0.10% max.; Copper (Cu): 0.50% max.; Iron (Fe): Balance.

Additionally, medical devices may also be composed partially or completely of biostable or bioerodible metals. Some metals are considered bioerodible since they tend to erode or corrode relatively rapidly when exposed to bodily fluids. Biostable metals refer to metals that are not bioerodible. Biostable metals have negligible erosion or corrosion rates when exposed to bodily fluids. Representative examples of biodegradable metals that may be used to fabricate stents may include, but are not limited to, magnesium, zinc, and iron. Biodegradable metals can be used in combination with biodegradable polymers.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of fabricating a stent, comprising:
   conveying a polymer gel comprising a bioabsorbable polymer dissolved in a solvent through an extruder, wherein the polymer gel allows coextrusion at a temperature below a melting point of the polymer;
   disposing a fluid into the extruder, wherein the fluid is supercritical in at least a portion of the extruder, the supercritical fluid being mixed or dispersed within the polymer, wherein a therapeutic agent is dissolved in the supercritical fluid, wherein the temperature is below a degradation temperature of the therapeutic agent;
   coextruding a tube comprising two layers, at least one layer being a porous layer formed from the polymer in the extruder, the porous structure of the layer being formed when the fluid becomes subcritical, wherein the therapeutic agent is impregnated within the porous layer; and
   forming a stent pattern in the coextruded tube.

2. The method of claim 1, wherein the porous layer is a luminal layer.

3. The method of claim 1, wherein the porous layer is an abluminal layer.

4. The method of claim 1, wherein a degradation temperature of the therapeutic agent is 80 to 100° C.

5. The method of claim 1, wherein pores of the porous structure are formed after the polymer exits the extruder and the fluid becomes subcritical.

6. The method of claim 1, wherein the solvent is removed from the gel after exiting the extruder.

7. A method of fabricating a stent, comprising:
   conveying a bioabsorbable polymer through an extruder, wherein the polymer is poly(L-lactide);
   disposing a fluid into the extruder, wherein the fluid is supercritical in at least a portion of the extruder, the supercritical fluid being mixed or dispersed within the polymer, wherein a therapeutic agent is dissolved in the supercritical fluid, wherein the polymer is above a melting temperature of the polymer;
   coextruding a tube comprising two layers, at least one layer being a porous layer formed from the polymer in the extruder, the porous structure of the layer being formed when the fluid becomes subcritical, wherein the therapeutic agent is impregnated within the porous layer; and
   forming a stent pattern in the coextruded tube.

* * * * *